United States Patent [19]
Dombrowski et al.

[11] Patent Number: 5,709,685
[45] Date of Patent: Jan. 20, 1998

[54] POSITIONABLE CLIP FOR PROVISIONALLY CAPTURING A COMPONENT ON A SPINAL ROD

[75] Inventors: Edmund T. Dombrowski, Redlands, Calif.; Michael C. Sherman, Memphis; Eddie Ray, III, Cordova, both of Tenn.

[73] Assignee: SDGI Holdings, Inc., Memphis, Tenn.

[21] Appl. No.: 651,967

[22] Filed: May 21, 1996

[51] Int. Cl.⁶ .................................................. A61B 17/70
[52] U.S. Cl. ................................... 606/61; 606/53; 24/336
[58] Field of Search .............................. 606/60, 61, 151, 606/157, 158; 24/329, 331, 336, 339

[56] References Cited

U.S. PATENT DOCUMENTS

| | | | |
|---|---|---|---|
| 593,978 | 11/1897 | Boehm | 224/462 |
| 3,680,818 | 8/1972 | Bujnowski et al. | 248/73 |
| 3,905,570 | 9/1975 | Nieuwveld | 248/71 |
| 3,907,239 | 9/1975 | Ehrlich | 248/229.26 |
| 4,451,257 | 5/1984 | Atchley | 604/119 |
| 5,059,193 | 10/1991 | Kuslich | 606/61 |
| 5,242,445 | 9/1993 | Ashman | 606/61 |
| 5,403,315 | 4/1995 | Ashman | 606/61 |
| 5,542,209 | 8/1996 | Sheu | 47/44 |

OTHER PUBLICATIONS

TSRH Spinal System Brochure, *Shaping the Future of Spinal Instrumentation;* Danek Group, Inc. 1993.

*Primary Examiner*—Michael Buiz
*Assistant Examiner*—David O. Reip
*Attorney, Agent, or Firm*—Woodard, Emhardt, Naughton, Moriarity & McNett

[57] ABSTRACT

A positionable clip is provided that is engageable on a spinal rod to capture a rod-borne component in a variable position on the rod. In one embodiment, the positionable clip includes a pair of clamping members, each including a pair of opposed arms configured for engaging the rod therebetween. A biasing hinge biases the arms together to grip the rod with sufficient force to maintain the position of the clip on the rod during manipulation of the rod. A bar connects the two clamping members to define a receiving space to receive a component that is disposed on the spinal rod. In one aspect, the bar includes a pressure surface such that a force applied to the pressure surface will cause the arms of the clamping members to displace apart to disengage from the spinal rod. The clip is configured so that this force can be applied by the component captured by the positional clip as the component is itself tightened onto the spinal rod.

19 Claims, 8 Drawing Sheets

POSITIONABLE CLIP FOR PROVISIONALLY CAPTURING A COMPONENT ON A SPINAL ROD

BACKGROUND OF THE INVENTION

This invention relates to orthopaedic implants, and particularly implant systems utilizing spinal rods spanning the length of the spine. More specifically, the invention concerns devices for provisionally positioning components, such as clamps, on a spinal rod during an implantation procedure.

Several techniques and systems have been developed for correcting and stabilizing spinal curves and for facilitating spinal fusion. In one type of system, a bendable rod is disposed longitudinally adjacent the vertebral column and is fixed to various vertebrae along the length of the spine by way of a number of fixation elements. A variety of fixation elements can be provided which are configured to engage specific portions of the vertebra. For instance, one such fixation element is a spinal compression/distraction hook. One type of spinal hook is used to anchor the rod by engaging the laminae of a vertebra. Another type of fixation element is a spinal screw, which includes cancellous threads for engagement within the vertebral bone.

Figure 1:
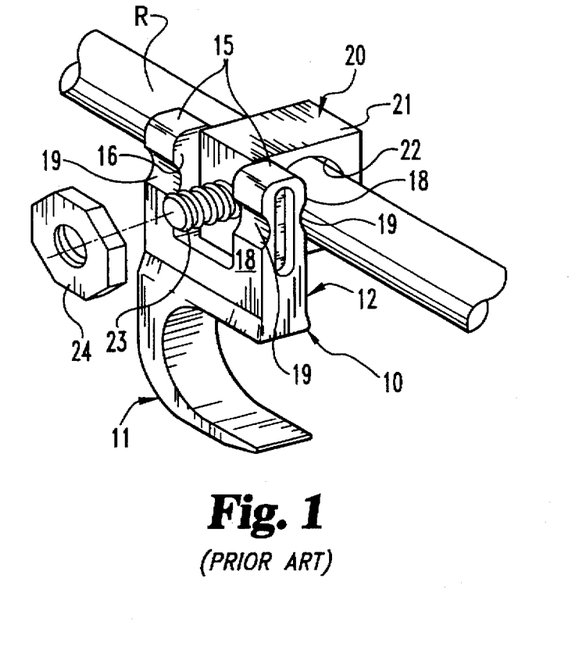
FIG. 1 is a perspective view of a spinal hook and rod construct of the prior art.

Rod-based spinal fixation systems can be external or internal. An example of an internal rod-type spinal fixation system is the TSRH® Spinal System sold by Danek Medical, Inc. In this system, a spinal hook, such as hook 10 shown in FIG. 1, is engaged to an elongated fixation rod R by way of an eyebolt assembly 20. The spinal hook 10 includes a hook portion 11 configured to engage a portion of a vertebra, and an integral head portion 12. The head portion in this particular hook of the TSRH® Spinal System includes a pair of posts 15 disposed apart from each other to form a U-shape yoke defining a slot 16 therebetween. The opposite faces 18 of the top portion 12 define a pair of coaxial grooves 19 that are configured to receive a portion of the spinal rod R.

The eyebolt assembly 20 includes an eyebolt body 21 defining an opening 22 through which the spinal rod R is received. A threaded post 23 extends from the body 21 for engagement with a threaded nut 24. In accordance with a use of the TSRH® Spinal System, the eyebolt body 21 is "pre-threaded" onto the spinal rod R so that the rod extends through the aperture 22 of a number of eyebolts 21 corresponding to each of the vertebral levels to be instrumented.

As depicted in FIG. 1, the spinal hook 10 is disposed with its yoke posts 15 straddling the body 21 of the eyebolt assembly 20, with the threaded post 23 and a portion of the body 21 extending through the slot 16. One surface 18 of the spinal hook is disposed against the rod R, specifically with the rod situated within a pair of coaxial grooves 19. The nut 24 can then be threaded onto the post 23 and against a surface 18 to clamp the spinal hook to the spinal rod in accordance with the "three-point shear clamp" aspect of the TSRH®System.

In a surgical procedure involving the TSRH® System, and particularly the eyebolt assembly 20 as depicted in FIG. 1, several eyebolt bodies 21 are threaded onto a spinal rod R prior to implantation into the patient's body. These eyebolts 21 are not fixed to the rod at that time since it is necessary to precisely locate and fix them only after the rod R has been placed within the body and the positions of the corresponding spinal hooks or screws have been determined. One difficulty posed by this type of arrangement, namely having a plurality of eyebolt bodies 21 loosely mounted on the spinal rod, is that these eyebolts can slide up and down along the rod and even fall off before the rod is placed within the patient. On the other hand, the eyebolts must have some capability of sliding along the rod to match the position of various vertebral fixation elements that may already be implanted in the spine. For example, a bone screw may already be threaded into a vertebral body which may require some adjustment of the position of an eyebolt to engage the bone screw. Likewise, many pre-planned positions for spinal hooks necessitate that the hooks are already situated in the appropriate vertebral level before the spinal rod R is implanted. It is therefore frequently necessary for the position of the eyebolt body along the spinal rod to be varied to mate with the appropriate vertebral fixation element.

Some prior systems incorporate set screws on the clamps or other components disposed on the spinal rod. While these set screws are very adequate to fix the components on the rod after they are suitably positioned in the body, they do not lend themselves to simply temporarily snugging the component on the rod during handling prior to implantation. One prior system, the Cotrel-Dubousset (CD) instrumentation, uses a blocker which is essentially a cylindrical element having a set screw in it. The cylindrical element is engaged with the component to be fixed onto the rod as a primary means for fixing the component to the rod. The set screw on the blocker can be used to provisionally position the cylindrical blocker on the spinal rod prior to final tightening. A discussion of this aspect of the CD System is found in U.S. Pat. No. 4,641,636 to Dr. Yves Paul Cotrel.

In practice, some surgeons have been known to string a suture through the opening 22 in the eyebolt body 21. The suture can be strung along several eyebolt assemblies 20 disposed along the length of the spinal rod R. The suture is sufficiently thick to provide some frictional contact between the rod and the opening of the eyebolt to provisionally retain the eyebolt on the rod under more delicate handling circumstances. However, the suture is not capable of providing sufficient gripping force to hold the eyebolt on the spinal rod under more rigorous handling during implantation.

Another approach has been to apply bone wax to the components to hold them onto the spinal rod. One disadvantage of this approach is that once the position of the component has been shifted on the spinal rod the provisional retention power of the bone wax is compromised.

Another approach is disclosed in U.S. Pat. No, 5,403,315 to Richard Ashman. This patent discloses a positionable spinal fixation device which is implemented in the eyebolt assembly itself. As discussed more fully in the '315 Patent, which disclosure is incorporate herein by reference, one embodiment uses a set screw extending through the threaded post of the eyebolt, such as threaded post 23 in FIG. 1 of the present application. This '315 Patent discusses additional embodiments that rely upon the eyebolt itself for both provisional and final clamping onto the rod. One difficulty with the positionable device disclosed in the '315 Patent is that it requires a more complicated eyebolt, instead of the use of an eyebolt of the type shown in FIG. 1. In addition, the concepts of the '315 Patent are not readily adaptable to other types of connectors or components engaged to a spinal rod, since the provisional clamping elements disclosed in the '315 Patent are only operable from within the eyebolt itself. Finally, the device shown in this prior patent generally requires that the provisional clamping element be retained within the construct after the system has been implanted within the patient.

There remains a need in the art of spinal surgery for a means for provisionally positioning a component on an elongated rod that resists movement of that component until it is finally attached to the rod. In addition, there is a need for such a device that can be used with virtually any type of component engaged on the spinal rod, and that can be readily removed.

SUMMARY OF THE INVENTION

In view of the need for provisional positioning of components during spinal surgery, the present invention contemplates several embodiments of a positionable clip that is removably engageable about a component disposed on an elongated rod. The provisional clips of the present invention provisionally capture a component at a position on the rod while allowing the position to be varied at any point during the surgical procedure. The provisional clips grip the elongated rod with enough force to prevent the clip and the captured component from freely sliding along the rod during manipulation of the rod.

In one embodiment, the positionable clip comprises a pair of clamping members, each including a pair of arms arranged to contact the elongated rod on opposite sides thereof. Each of said clamping members includes means for biasing the pair of arms together to provide a gripping force on the rod when the rod is disposed between the pair of arms. The clip also comprises a bar connecting the pair of clamping members in spaced apart relation, with a length between the pair of clamping members sufficient to capture a component engaged on the elongated rod between the clamping members.

In one specific embodiment, the means for biasing the arms together includes the pair of arms of each of the clamping members being formed of a resilient material. The resilient material allows the pair of arms to resiliently deflect between a first position in which the arms are gripping the rod and a second position in which the arms are disposed apart sufficient for the rod to pass between the arms. In another specific embodiment, the means for biasing the arms together includes a resilient hinge between the pair of arms and the bar. In this specific embodiment, the hinge is resiliently openable to move the arms between the rod gripping position and the rod release position.

In this preferred embodiment, the pair of arms of each of the pair of clamping members defines a clamping surface directed toward the rod. The clamping surface is configured to substantially conform to the outer surface of the rod. In the case of a cylindrical spinal rod, the rod engaging surface of the arms is partially cylindrical with substantially the same diameter as the spinal rod.

In a further aspect of the invention, the positionable clip includes a lever arm attached to the bar opposite the pair of clamping members. The lever arm is operable to remove the pair of clamping members from the rod when the rod is disposed between the pair of arms of the clamping members. In one specific embodiment, the lever arm is configured so that force applied to the lever arm creates a bending moment to disengage the arms of the clamping members from the spinal rod.

The positionable clip of the present invention also contemplates means to disengage the clip from the spinal rod by operation of the component captured on the rod by the clip. In one embodiment, the pair of arms of each of the clamping members each includes a pressure surface defined at the free end of the arms. When a force is applied to the pressure surface of each of the arms, the free ends of the arms and the clamping surface slide around the rod to deflect the pair of arms apart against the means for biasing. In one use of the inventive clip, the clip is engaged about a clamp disposed on the rod. As the clamp is tightened onto the rod, a surface of the clamp pushes against the pressure surface of the clamping arms of the positionable clip.

In an alternative specific embodiment, the pressure surface is disposed on the bar between the clamping members and facing away from the bar. A force applied to the bar pressure surface causes the clamping surface of each of the arms to slide around the rod to deflect the pair of arms apart against the means for biasing.

Preferably, the positionable clip is formed or a radiolucent material, most preferably a plastic. In some instances, verification of the position of the clip within the patient is desirable. In another specific aspect of the invention, a radio-opaque verification pin is disposed within the bar portion of the clip. This verification pin can be verified by A-P radiograph, thereby providing an indication of the position of the clip on the spinal rod.

The present invention also contemplates another embodiment of the positionable clip that comprises a single clamping member including a pair of arms arranged to contact the elongated rod on opposite sides thereof, and means for biasing the pair of arms together to provide a gripping force on the rod when the rod is engaged between the pair of arms. This clip includes a bar connected to the clamping member and having a length extending substantially parallel to the rod when the rod is engaged between the pair of arms. The bar includes a surface directed toward rod when the rod is engaged between the arms, which surface is configured to contact the component to capture the component in a position on the rod. In one aspect of this embodiment of the positionable clip, the bar is resiliently biased toward the rod when the rod is engaged between the pair of arms, so that the bar applies a clamping force against the component.

In a further feature of this embodiment, the means for biasing the arms of the clamping member includes a resilient hinge connected between the pair of arms, and the clamping member further includes a pair of tabs extending from a corresponding one of the pair of arms. The tabs arranged relative to the resilient hinge to deflect the hinge when the tabs are depressed toward each other, whereby the pair of arms are disengaged from the rod.

In yet another embodiment of the invention, a positionable clip comprises a bar having a length between first and second ends, the length sized to span a length of the component along the elongated rod when the component is disposed thereon. The clip further comprises a pair of upper arms, one each connected to the bar at a respective one of the first and second ends, and each defining a clamping surface directed toward the rod when the positionable clip is capturing a component on the rod. In one aspect of this embodiment, the clip comprises a lower arm connected to the bar between the first and second ends, the lower arm defining a lower clamping surface directed toward the component when the component is disposed on the elongated rod. Biasing means are provided for biasing the pair of upper arms towards the lower arm to provide a gripping force on the elongated rod engaged therebetween.

In one specific feature of this embodiment, the clip can include a lever arm connected to the bar and operable against the biasing means to disengage the upper arms and the lower arm from the elongated rod. In a further specific aspect, the clamping surface of each of the pair of upper arms is sized to contact at least a third of the circumference of the elongated rod, and most preferably about half way around the rod circumference.

One object of the present invention is to provide a device that can temporarily retain or capture a component on a spinal rod during manipulation and implantation of the rod in a human patient. Another object is achieved by features of the invention that allow the device to hold its position on the rod and to be moved to a new position as necessary during the surgical procedure.

Another object of the invention is to provide a device that need not remain within the patient once the spinal fixation assembly is finally implanted. A further object is embodied in aspects of the invention that allow the device to be disengaged from the spinal rod by operation of the component to be captured on the rod.

Each of these objects are addressed by the present invention and manifest themselves as important benefits to surgeons in the field of spinal surgery. These benefits include the capability to provisionally fix the position of a component on a spinal rod during even the most rigorous manipulation of the rod; the ability to readily adjust the position of the component as required to allow mating of the rod-borne component with vertebral fixation elements; and the capability of removing the device once the spinal rod and fixation system are finally positioned and implanted within the patient. Other objects and benefits of the present invention can be readily discerned from the following written description of the invention together with the accompanying figures.

DESCRIPTION OF THE PREFERRED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention concerns a positionable clip that is engageable about a component disposed on an elongated spinal rod. This positionable clip provisionally captures the component at a given position on the rod to help maintain the orientation of the components as the rod is manipulated prior to and during implantation in a human patient. In addition, the positionable clip is slidable to different positions on the rod as necessary to reposition the components disposed on the rod, while still maintaining an adequate clamping force on the rod to hold the component at the new position. In a further feature of the positionable clips according to the present invention, the clips can be readily disengaged from the spinal rod and removed from the surgical site. Most preferably, the clips of this invention can be at least partially disengaged from the spinal rod by operation of the captured component itself.

Figure 2:
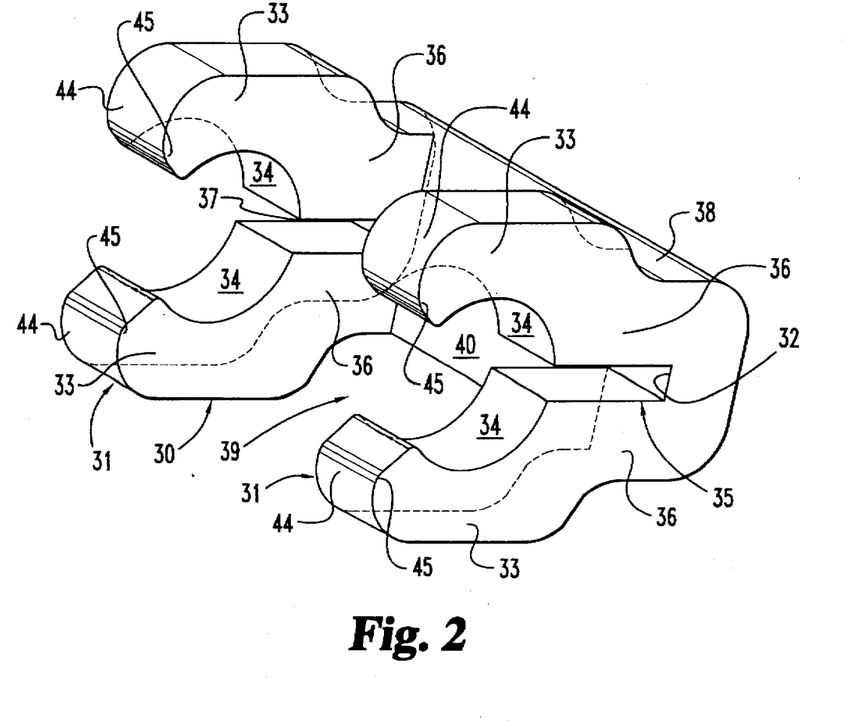
FIG. 2 is a perspective view of a positionable clip according to one embodiment of the present invention.
Figure 3:
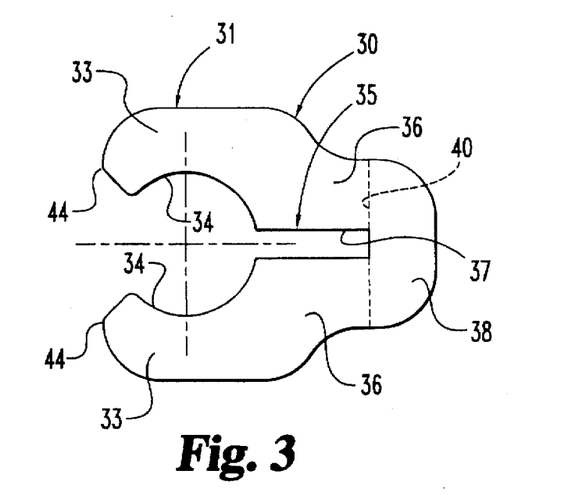
FIG. 3 is an end elevational view of the positionable clip shown in FIG. 2.

In accordance with a first embodiment of the present invention, a positionable clip 30 is shown in FIGS. 2,3 that comprises a pair of clamping members 31. Each of the clamping members includes a pair of arms 33 defining a clamping surface 34. The clamping surface is arranged to engage the spinal rod when the positionable clip 30 is clamped onto the rod. Preferably, the clamping surfaces 34 are partially cylindrical to correspond to the outer cylindrical surface of the elongated spinal rod.

The positionable clip 30 includes a biasing means 35 which is configured to bias the arms 33 toward each other. This biasing means 35 permits the arms to provide a clamping force on the rod to hold the clip 30 on the rod as the rod is manipulated and implanted within the patient. Preferably, the biasing means provides only as much clamping force through the arms 33 as is necessary to keep the positionable clip 30 and the rod component that it captures from freely sliding up and down the spinal rod. The clamping force generated by the biasing means 35 is also preferably sufficient to hold the position of the clip and its captured component during even the harshest manipulations of the spinal rod during the surgical procedure. On the other hand, the biasing means preferably does not provide so much clamping force on the rod through the arms 33 that the clip 30 cannot be easily slid along the rod to reposition the clip and its captured component.

The biasing means 35, while biasing the arms 33 together, is also preferably readily counteracted to permit spreading of the arms 33 to disengage the positionable clip 30 from the spinal rod. In one specific embodiment, the biasing means 35 constitutes the arms 33 being formed of a resilient material that can be deflected or deformed as the rod is slid outwardly along the clamping surfaces 34. In other words, the biasing means 35 can include resilient arms 33 that can be urged apart by an outward movement of the spinal rod away from the clamping surfaces 34.

In a further specific embodiment, the biasing means 35 includes a hinge portion 36 integral with each of the arms 33. The hinge portions are separated by hinge slot 37, which slot opens and closes as the arms 33 are pushed outward away from each other or together toward each other.

Figure 4:
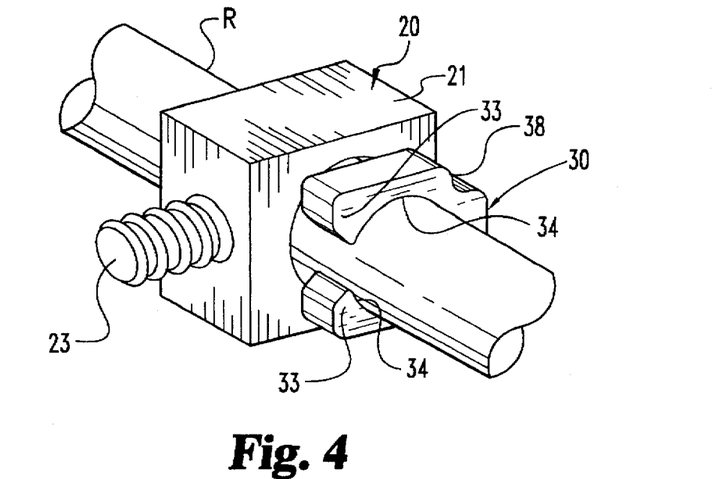
FIG. 4 is a perspective view of a rod having an eyebolt disposed thereon with the positionable clip of FIGS. 2,3 engaged about the eyebolt on the rod.
Figure 5:
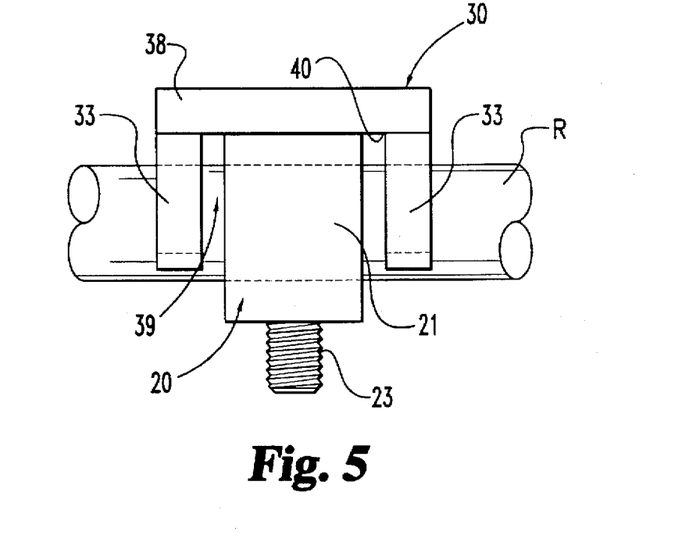
FIG. 5 is a top elevational view of the construct shown in FIG. 4.

The positionable clip 30 shown in FIGS. 2,3 also includes a bar 38 spanning between and connecting the two clamping members 31. The bar 38 and the clamping members 31 define a receiving space 39 therebetween which is sized to receive a particular component engaged to a spinal rod. For example, as shown in FIGS. 4 and 5, the positionable clip 30 is shown mounted on a spinal rod R. An eyebolt 20, which is identical to the eyebolt depicted in FIG. 1, is disposed on the rod R in the receiving space 39 of the positionable clip 30. Specifically, the eyebolt 20 is situated between the arms 33 of the clamping members 31 and is bordered on one side by the bar 38. The bar 38 includes a bar pressure surface 40 which is in contact with the eyebolt body 21.

As depicted in FIGS. 4 and 5, the positionable clip 30 is shown capturing an eyebolt body 21 on the rod R. It is understood that the eyebolt body 21 would normally freely slide along the longitudinal length of the rod R. However, the positionable clip 30 is engaged to the rod by way of the clamping force generated by the arms 33 and their biasing means 35. The arms 33 provide a sufficient gripping force to resist movement of the eyebolt body 21 along the rod, even under the most severe manipulations of the spinal rod R. On the other hand, the clamping surface 34 engaging the outer cylindrical surface of the rod R is capable of sliding along the rod R without damaging the rod. The arms 33 can then provide the same clamping force at the new location of the eyebolt body 21. This feature allows ready adjustment of the position of the eyebolt 20 at any point during the manipulation and implantation of the spinal rod R.

Figure 6:
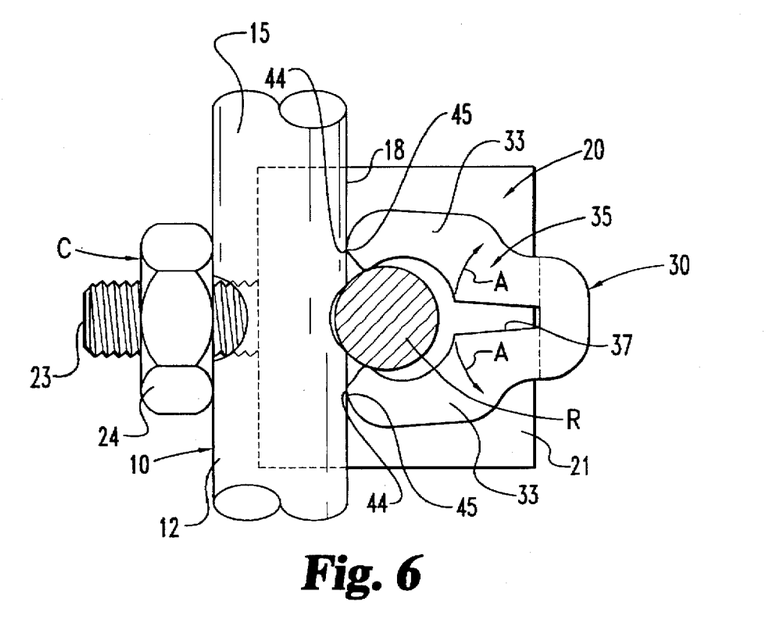
FIG. 6 is a side elevational view of the construct shown in FIGS. 4 and 5 with the addition of the head of a spinal hook engaged to the eyebolt and spinal rod, in which the positionable clip is shown partially disengaged from the spinal rod.

It is understood that several of these positionable clips 30 can be engaged about various components disposed along a spinal rod R prior to implantation. In a typical TSRH® configuration, several eyebolts, such as the eyebolt 20, would be located on the spinal rod. In one particular application, the eyebolt 20 could be used to engage a spinal hook, such as hook 10 shown in FIG. 1. As shown in FIG. 6, the head portion 12 of the hook 10 can be disposed about the eyebolt body 21. The nut 24 is then threaded along the threaded post 23 to press the head 12 of the hook against the spinal rod R.

In one specific embodiment of the positionable clip 30, the arms 33 include an arm pressure surface 44 at their free end 45. As the head 12 of the hook 10 is pushed toward the rod R by tightening of the nut 24, the surface 18 of the spinal hook pushes against the arm pressure surface 44 of each of the arms 33. This pushing force is in the direction of the arrow C shown at the left of FIG. 6. As this force C is applied through the surface 18 of the spinal hook 10 against the arm pressure surfaces 44, the arms 33 are forced to ride along the outer surface of the spinal rod R, against the force of the biasing means 35 to thereby pivot the arms 33 in the direction of the arrows A. In the specific embodiment depicted in FIG. 6, this pivoting movement designated by the arrows A of the arms 33 serves to open the hinge slot 37 so that the space between the free ends 45 of the arms increases enough to allow the spinal rod R to pass between the arms. Preferably, the location of the arm pressure surface 48, or more particularly the length of the arms 33, is calibrated so that when the spinal hook 10 is fully tightened between the nut 24 and the rod R, the free ends 45 of the arms 33 are still in contact with the spinal rod. Preferably, these ends contact the spinal rod at nearly diametrically opposite positions on the rod so that a simple pulling force applied to the positionable clip 30 will allow ready removal of the clip.

In another specific embodiment, the length of the arms 33 and the orientation of the arm pressure surfaces 44 can be configured so that when the nut 24 is fully tightened down onto the hook 10 and rod R, the free ends 45 of the arms 33 slide easily off of the rod R.

Figure 7:
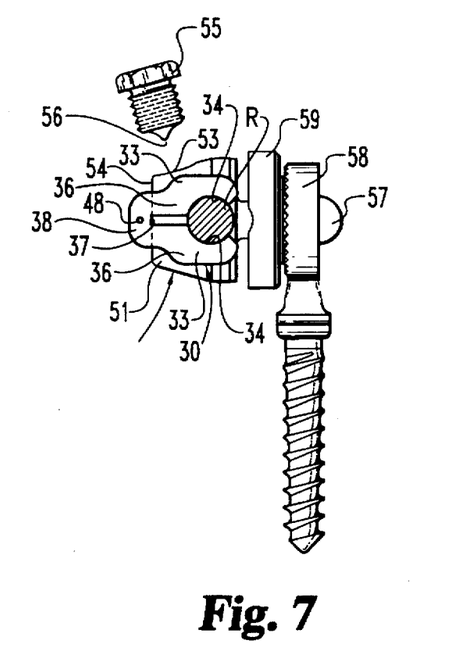
FIG. 7 is a side elevational view of a further construct for a top-tightening variable angle screw, shown with the positionable clip, as shown in FIGS. 2,3, engaged to the spinal rod.
Figure 8:
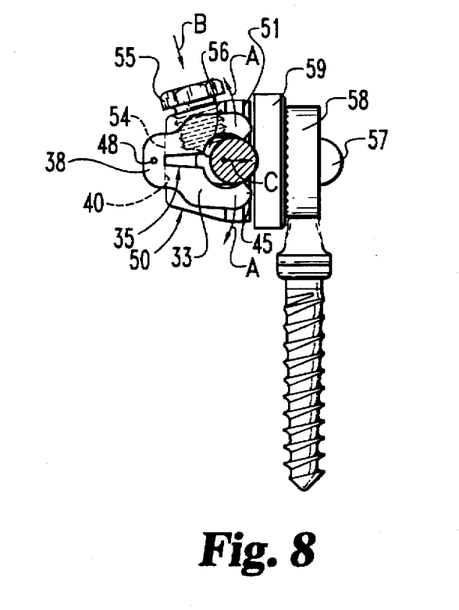
FIG. 8 is a side elevational view of the construct shown in FIG. 7 with the positionable clip partially disengaged from the spinal rod as the set screw is tightened into the top-tightening assembly.
Figure 9:
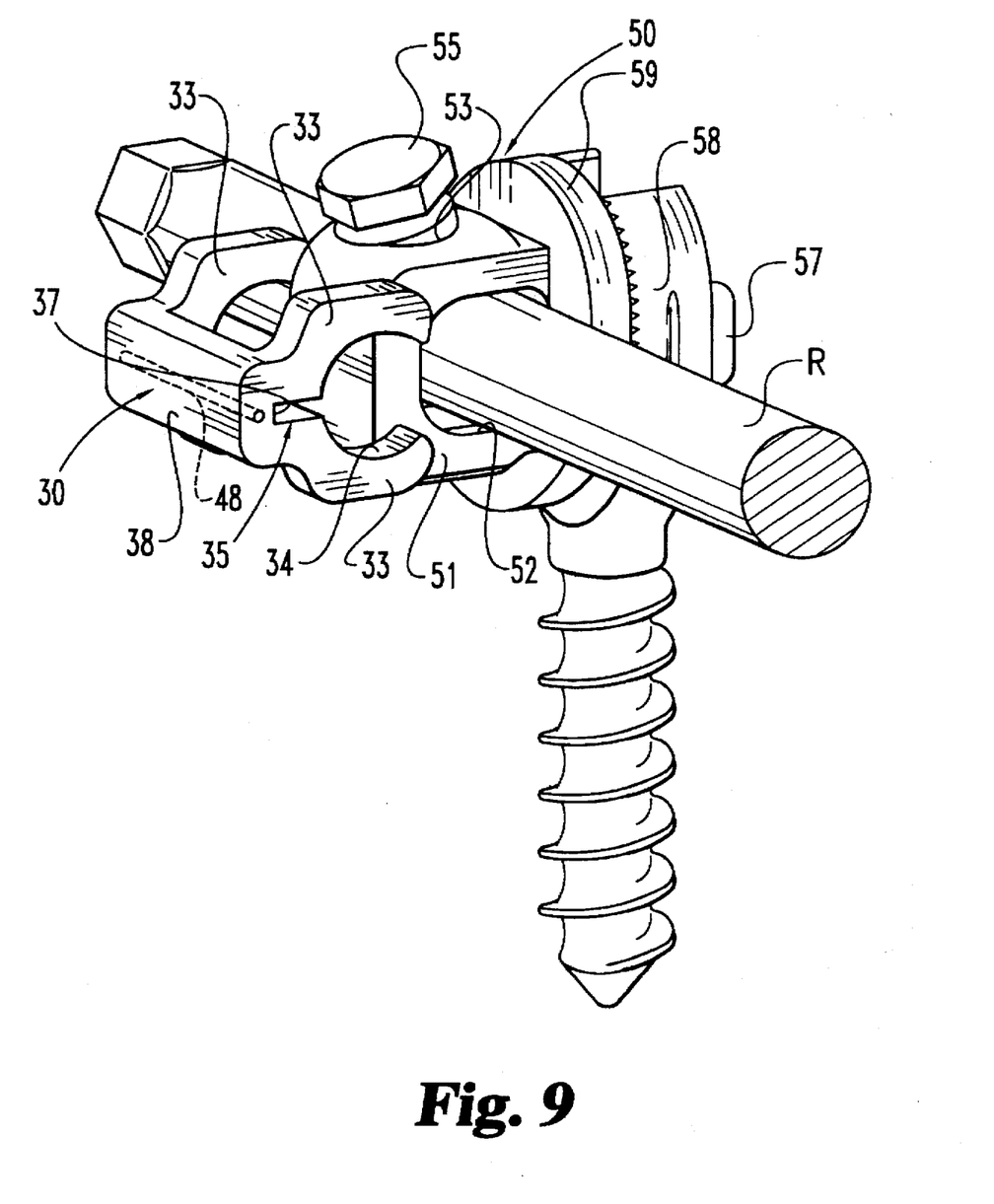
FIG. 9 is a perspective view of the top-tightening variable angle screw construct shown fully tightened after which the positionable clip is disengaged from the spinal rod.

The positionable clip 30 according to the present embodiment can be used with a different component engaged to a spinal rod R. In particular, one such component can be a clamp assembly 50, as shown in FIGS. 7–9, constituting part of a top-tightening variable angle screw assembly. The clamp assembly 50 is used to engage a variable angle washer 59 and variable angle screw 58 to the spinal rod R. This particular system engaged to the spinal rod R is described more fully in U.S. Pat. No. 5,282,801, issued on Feb. 1, 1994 to Mike Sherman entitled "Top-Tightening Clamp Assembly for a Spinal Fixation System". The disclosure of this '801 Patent is incorporated herein as it pertains to the structure and operation of the clamp assembly 50 and the components 58 and 59.

For clarity, the clamp assembly includes a clamp body 51 which defines a rod opening 52 through which the spinal rod R passes. A set screw bore 53 passes through the clamp body 51 to intersect the rod opening 52. The body 51 also includes a back surface 54 against which the bar 38 of the positionable clip 30 contacts. A set screw 55 is threaded into the set screw bore 53 so that its tip 56 contacts the spinal rod R. The clamp assembly 50 further includes a T-bar 57 which provides a surface against which the variable angle screw 58 is clamped.

As shown in FIG. 7, the positionable clip 30 is depicted clamped about the body 51 of the clamp assembly 50. In particular, the clamping surface 34 of the arms 33 is clamped onto the outer surface of the spinal rod R with sufficient pressure to hold the clamp body 51 in its position on the spinal rod R. As shown in FIG. 8, the set screw 55 is driven into the bore 53 in the direction of the arrow B. As the set screw is threaded into the bore, the tip 56 pushes on the spinal rod R to force it in the direction of the arrow C. As the spinal rod R is moved in the direction C, it bears against the washer 59, which presses the variable angle bone screw 58 against the T-bar 57.

At the same time the spinal rod R is moving in the direction C, the clamp body 51 is, in effect, moving in the opposite direction by virtue of the driving force B applied by the set screw 55. More specifically, the back surface 54 of the clamp body 51 is pushed against the bar pressure surface 40 of the positionable clip 30. As the set screw 55 is fully tightened into the set screw bore 53, the back surface 54 continues to push against the bar pressure surface 40 of the positionable clip 30 which forces the free ends 45 of the arms 33 to move apart in the direction of the arrows A, as shown in FIG. 8.

Again, as with the specific application shown in FIG. 6, the movement of the clamp body 51 in relation to the length of the arms 33 and the location of the free ends 45 is calibrated so that the free ends 45 remain in contact with the spinal rod R but on substantially diametrically opposite points on the rod so that the clip 30 can be easily plucked off of the rod. Alternatively, this length of the arms relative to the movement of the clamp body 51 can be calibrated so that the free ends 45 of the arms 33 fall clear of the rod as the rod passes through the enlarged opening between the arms 33. In this final configuration, the clamp assembly 50 firmly affixes the bone screw 58 through the spinal rod R while the clamp assembly 30 is free of the spinal rod R, as shown in FIG. 9.

In one specific embodiment of the positionable clip 30, the clip is formed of a radio-opaque plastic, such as DELRIN®. However, under some circumstances it may be desirable to verify the position of the clip by radiograph during certain surgical procedures. In these circumstances, a radio-opaque verification pin 48 may be inserted into a bore defined in the bar 38, as depicted in FIGS. 7–9. The position of the verification pin 48, and consequently the clip 30, can be ascertained from an A–P radiograph. Verification of the verification pin from a lateral view may be difficult due to the presence of the spinal rod R, unless the verification pin is formed of a material having a noticeably different opacity than the spinal rod R.

Preferably, the positionable clip 30 is formed of a resilient and readily deflectable plastic that is capable of being restored to its original configuration without fracture or failure. Since the positionable clip 30 is not intended to remain within the patient, it need not be formed of a biocompatible material. In addition, the clip may be formed of a sterilizable material for reuse, or of a cheaper material for disposal after use.

In one specific embodiment of the clip 30, the clip is sized to engage a ¼ inch stainless steel spinal rod. In this configuration, the arms and hinge portions 36 extend a dimension of approximately 0.312 inches from the bar. The bar has a length of approximately 0.5 inches to accommodate a component such as the clamp assembly 50 shown in FIGS. 7–9. The clamping surfaces 34 of each of the arms of the positionable clip is circular and defined at a diameter of preferably 0.235 inches. In this specific embodiment, the bar 38 has a width of 0.20 inches and the hinge slot 37 of the biasing means 35 has a width of 0.035 inches.

Figure 10:
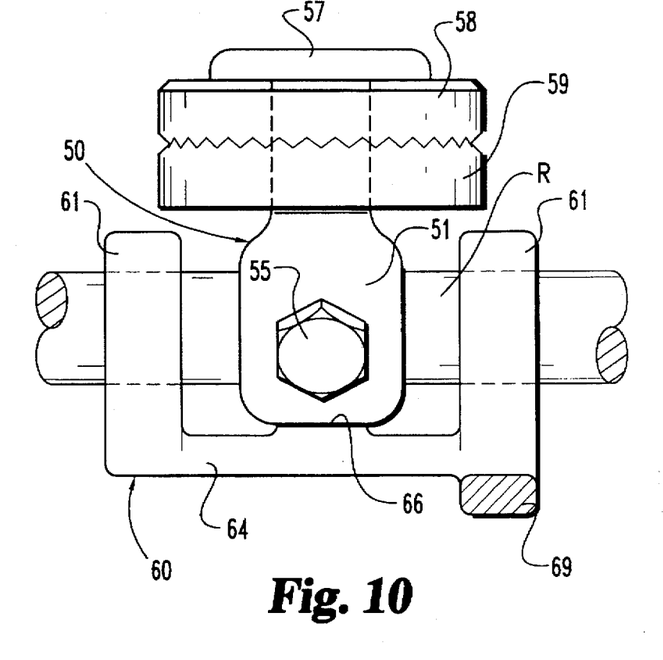
FIG. 10 is a top elevational view of a further embodiment of the positionable clip of the present invention.

In another embodiment of the invention, a positionable clip 60 includes a pair of rod engaging arms 61 situated at the opposite ends of a bar 64. The arms are disposed apart a sufficient distance to capture either a clamp body 51 of a clamp assembly 50, or capture the washer 59 of the assembly 50, as shown in FIG. 10. As shown more clearly in FIG. 11, the rod engaging arms 61 define a rod clamp surface 62. In contrast to the previous embodiment in which two arms were disposed on opposite sides of the rod adjacent each other, the arms 61 do not have an equivalent arm facing them on an opposite side of the spinal rod R. Instead, the rod clamp surface 62 of the arms 61 is calibrated to extend in contact with at least ⅓ of the circumference of the spinal rod R. In a most preferred embodiment, the arms 61 include an arm extension 63 which extends the rod clamp surface 62 to contact about half of the circumference of the rod R.

Figure 11:
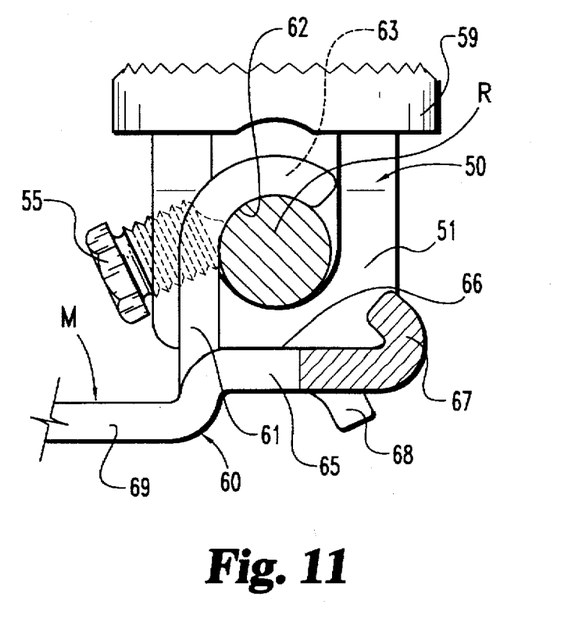
FIG. 11 is a side elevational view of the additional embodiment of the positionable clip shown in FIG. 10.

To provide a clamping force in opposition to the arms 61, the bar 64 can include a lower arm 65 projecting therefrom. The lower arm 65 includes a body clamp surface 66 that is configured to engage the body 51 of the clamp assembly 50. In one specific embodiment, the lower arm 65 terminates in an arm extension 67 that is configured to wrap around a portion of the clamp body 51. In a further specific embodiment, the lower arm 65 can include a second arm extension 68 that turns away from the clamp body, so that the lower arm 65 operates in the form of a spring to press the body clamp surface 66 against the clamp body 51.

The positionable clip 60 can also include a lever arm 69 projecting from the bar 64. The lever arm can be used to manually disengage the positionable clip 60 from the spinal rod R by exerting a moment force on the lever arm directed away from the upper arms 61. Specifically, a moment force designated by the arrow labeled M in FIG. 11 can be applied to the end of the lever arm 69, which force is reacted by pressure from the lower arm body clamp surface 66 against the clamp body 51. As the moment force M is continuously applied to lever arm 69, the body clamp surface 66 of the lower arm 65 acts as a fulcrum to disengage the upper arms 61 from around the spinal rod R. In this circumstance, the rod clamp surfaces 62 slide around the outer circumference of the rod to open the arms 61 and disengage them from the rod.

Alternatively, the positionable clip 60 can be disengaged from the rod R in the same manner as the embodiment and application shown in FIGS. 7–9. In particular, as the set screw 55 is tightened into the clamp body 51, it pushes the rod R toward the washer 59. At the same time, the back surface of the clamp body 51 pushes back against the body clamp surface 66 of the lower arm 65. As the set screw 55 is further tightened into the clamp body, the rod R gradually disengages from the upper arms 61, permitting removal of the positionable clip 60.

Figure 12:
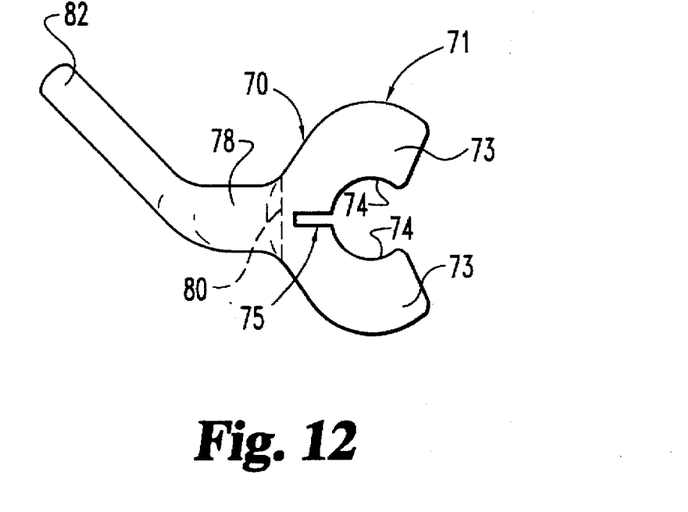
FIG. 12 is a side elevational view of a positionable clip of a third embodiment of the present invention.
Figure 13:
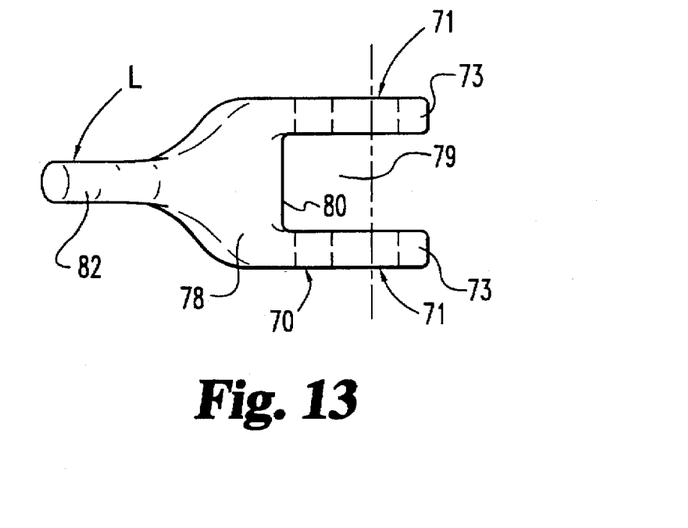
FIG. 13 is a top elevational view of the positionable clip shown in FIG. 12.

A further embodiment of the present invention is shown in FIGS. 12 and 13. In particular, a positionable clip 70 includes a pair of clamping members 71, each formed by a pair of opposing arms 73. The arms define clamping surfaces 74 which are configured to engage a spinal rod, in the manner of positionable clip 30 shown in FIGS. 2–3. In addition, the clip 70 includes biasing means 75 which can be of the same type as the biasing means 35 in the previous embodiment.

The positionable clip 70 also includes a bar 78 to which ends the arms 73 are attached. The bar 78 and the clamping member 71 define a receiving space 79 for capturing a component at a position on a spinal rod. The bar 78 also includes a bar pressure surface 80 which acts in the same manner as bar pressure surface 40 of the positionable clip 30. In this embodiment, the clip 70 includes a lever arm 82 extending from the bar 78. This lever arm can be moved longitudinally in the direction of the arrow L to disengage the one set of arms 73 from the spinal rod, to ultimately disengage the entire clip from the rod.

Figure 14:
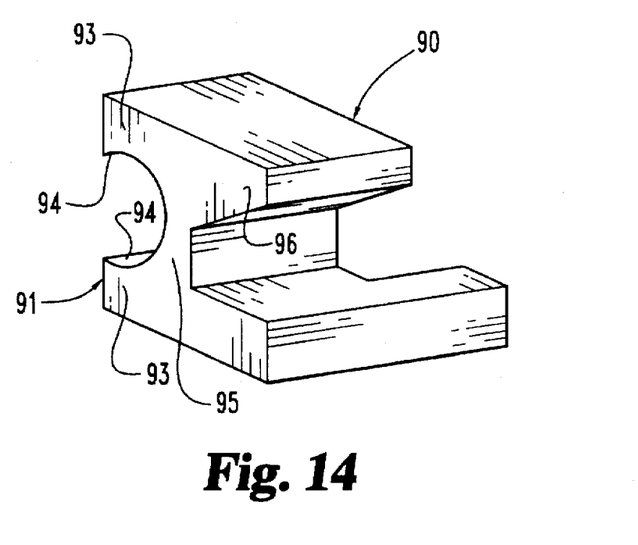
FIG. 14 is a top perspective view of a positionable clip in accordance with a further embodiment of the present invention.
Figure 15:
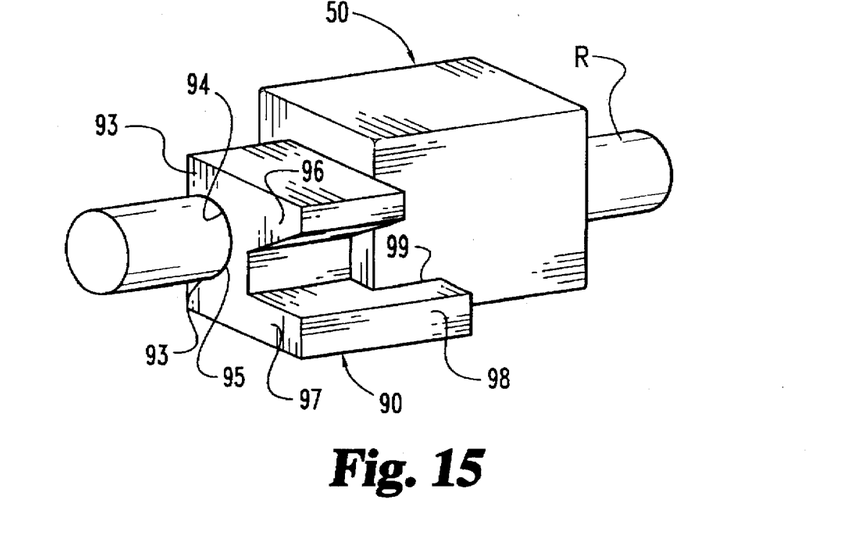
FIG. 15 shows a positionable clip according to that shown in FIG. 14 engaged on a spinal rod and capturing a component onto the rod.

In a further embodiment of the invention shown in FIGS. 14 and 15, a positionable clip 90 includes a clamping member 91 defined by a pair of opposed arms 93. The arms form a clamping surface 94 which is configured to engage a spinal rod R therebetween. The clip 90 also includes a resilient hinge 95 formed between the two arms 92. The hinge also includes a pair of opening tabs 96 and 97, each of which are integral with a corresponding one of the arms 93. As shown in FIGS. 14 and 15, the opening tabs project away from the arms on opposite sides of the resilient hinge 95. The arms 93 can be moved apart by depressing the two tabs 96 and 97 toward each other, thereby flexing the resilient hinge 95.

The positionable clip 90 further includes a bar 98 extending from the clamping member 91. In this specific embodiment, the positionable clip includes but a single bar and a single clamping member 91, so that the clip does not fully capture the component, such as component 50 in FIG. 15, on the spinal rod. Instead, the bar 98 includes a contact surface 99 which is configured for a frictional engagement with the component 50. In addition, the bar 98 can be formed of a resilient material to maintain a constant pressure on the component 50 to prevent it from sliding along the length of the spinal rod R.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A positionable clip engageable about a component disposed on an elongated rod for provisionally capturing the component at a position on the rod, said positionable clip comprising:

a pair of clamping members, each including a pair of arms arranged to simultaneously contact the elongated rod on substantially opposite sides thereof, each of said clamping members also including means for biasing said pair of arms together to provide a gripping force on the rod when the rod is disposed between said pair of arms; and a bar connecting said pair of clamping members in spaced apart relation, said bar having a length between said pair of clamping members sufficient to capture a component engaged on the elongated rod between said clamping members when the rod is disposed between said pair of arms of each of said pair of clamping members; wherein said means for biasing said arms together includes a resilient hinge between said pair of arms and said bar, whereby said hinge is resiliently openable to move said arms between a first position in which said arms are gripping the rod and a second position in which said arms are disposed apart sufficient for the rod to pass between said arms.

2. The positionable clip according to claim 1, wherein said means for biasing said arms together includes said pair of arms of each of said clamping members being formed of a resilient material, whereby said pair of arms is resiliently deflectable between a first position in which said arms are gripping the rod and a second position in which said arms are disposed apart sufficient for the rod to pass between said arms.

3. The positionable clip according to claim 1, wherein said resilient hinge includes a pair of hinge portions connecting a corresponding one of said pair of arms to said bar, said pair of hinge portions defining a slot therebetween.

4. The positionable clip according to claim 1, wherein each of said pair of arms of each of said pair of clamping members defines a clamping surface directed toward the rod when the rod is engaged between said pair of arms, said clamping surface being configured to substantially conform to the outer surface of the rod.

5. The positionable clip according to claim 4, wherein each of said pair of arms of each of said pair of clamping members further includes:

a first end connected to said bar; and an opposite free second end, said second end defining a pressure surface facing away from said bar; and wherein said clamping surface of each of said pair of arms extends from said first end to said second end and is configured to surround at least a portion of the rod opposite said bar, whereby a force applied to said pressure surface of each of said arms causes said clamping surface to slide around the rod to deflect said pair of arms apart against said means for biasing.

6. The positionable clip according to claim 4, wherein:

said clamping surface of each of said pair of arms is configured to surround at least a portion of the rod opposite said bar; and said bar includes a bar pressure surface facing away from said bar and disposed between said pair of clamping members, whereby a force applied to said bar pressure surface causes said clamping surface of each of said arms to slide around the rod to deflect said pair of arms apart against said means for biasing.

7. The positionable clip according to claim 4, wherein said clamping surface includes a surface that is slidable along the rod.

8. The positionable clip according to claim 1, further comprising a lever arm attached to said bar opposite said pair of clamping members, said lever arm operable to remove said pair of clamping members from the rod when the rod is disposed between said pair of arms of said clamping members.

9. The positionable clip according to claim 1, wherein said clip is formed of a radiolucent material.

10. The positionable clip according to claim 9, further comprising a radio-opaque pin disposed within said bar.

11. A positionable clip engageable about a component disposed on an elongated rod for provisionally capturing the component at a position on the rod, said positionable clip comprising:

a clamping member including a pair of arms arranged to simultaneously contact the elongated rod on substantially opposite sides thereof, and means for biasing said pair of arms together to provide a gripping force on the rod when the rod is disposed between said pair of arms; and a bar connected to said clamping member and having a length extending substantially parallel to the rod when the rod is disposed between said pair of arms, said bar including a surface directed toward the rod disposed apart in relation to the rod when the rod is disposed between said arms, said surface configured to contact the component to capture the component in a position on the rod; wherein said means for biasing includes a resilient hinge connected between said pair of arms.

12. The positionable clip according to claim 11, wherein said bar is resiliently biased toward the rod when the rod is engaged between said pair of arms, whereby said bar applies a clamping force against the component.

13. The positionable clip according to claim 11, wherein said clamping member further includes a pair of tabs extending from a corresponding one of said pair of arms, said tabs arranged relative to said resilient hinge to deflect said hinge when said tabs are depressed toward each other, whereby said pair of arms are disengaged from said rod.

14. The positionable clip according to claim 13, wherein said bar constitutes one of said pair of tabs.

15. A positionable clip engageable about a component disposed on an elongated rod for provisionally capturing the component at a position on the rod, said positionable clip comprising:

a bar having a length between first and second ends, said length sized to span a length of the component along the elongated rod when the component is disposed thereon;

a pair of upper arms, one each connected to said bar at a respective one of said first and second ends, each of said upper arms defining a clamping surface directed toward the rod when said positionable clip is capturing a component on the rod;

a lower arm connected to said bar between said first and second ends, said lower arm defining a lower clamping surface directed toward the component when the component is disposed on the elongated rod; and biasing means for biasing said pair of upper arms towards said lower arm to provide a gripping force on the elongated rod and the component engaged between said upper arms and said lower arm; wherein said lower arm includes a first end connected to said bar and a free second end, wherein said first end defines a pressure surface facing the component disposed on the rod when said positional clip is capturing a component on the rod, whereby a force applied to said pressure surface causes said clamping surface of each of said pair of upper arms to slide around the rod to deflect said pair of upper arms against said means for biasing.

16. The positionable clip according to claim 15, further including a lever arm connected to said bar and operable against said biasing means to disengage said upper arms and said lower arm from the elongated rod.

17. The positionable clip according to claim 15, wherein said clamping surface of each of said pair of upper arms is sized to contact at least a third of the circumference of the elongated rod.

18. The positionable clip according to claim 15, wherein said means for biasing includes said pair of upper arms being formed of a resilient material, whereby said pair of upper arms is resiliently deflectable between a first position in which said upper arms are pressing the rod toward said lower arm and a second position in which said upper arms are disposed apart from said lower arm sufficient for the rod to pass between said upper arms and the component contacting said lower clamping surface of said lower arm.

19. The positionable clip according to claim 15, wherein said means for biasing includes said lower arm being formed of a resilient material, whereby said lower arm is resiliently deflectable between a first position in which said lower arm is pressing the component towards the rod and the rod against said pair of upper arms and a second position in which said lower arm is disposed apart from said pair of upper arms sufficient for the rod to pass between said upper arms and the component contacting said lower clamping surface of said lower arm.

* * * * *